(12) United States Patent
Kim et al.

(10) Patent No.: US 12,329,518 B2
(45) Date of Patent: Jun. 17, 2025

(54) AUDITORY ABILITY TEST DEVICE AND METHOD BASED ON OPTICAL COHERENCE TOMOGRAPHY

(71) Applicant: KYUNGPOOK NATIONAL UNIVERSITY INDUSTRY-ACADEMIC COOPERATION FOUNDATION, Daegu (KR)

(72) Inventors: Jeehyun Kim, Daegu (KR); Pilun Kim, Daegu (KR); Mansik Jeon, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1019 days.

(21) Appl. No.: 17/276,695

(22) PCT Filed: Dec. 13, 2019

(86) PCT No.: PCT/KR2019/017659
§ 371 (c)(1),
(2) Date: Mar. 16, 2021

(87) PCT Pub. No.: WO2020/159075
PCT Pub. Date: Aug. 6, 2020

(65) Prior Publication Data
US 2022/0022780 A1    Jan. 27, 2022

(30) Foreign Application Priority Data

Jan. 28, 2019   (KR) .................. 10-2019-0010487
Apr. 2, 2019    (KR) .................. 10-2019-0038346

(51) Int. Cl.
*A61B 5/00*   (2006.01)
*A61B 5/12*   (2006.01)

(52) U.S. Cl.
CPC ............ *A61B 5/125* (2013.01); *A61B 5/0066* (2013.01); *A61B 5/6817* (2013.01)

(58) Field of Classification Search
None
See application file for complete search history.

(56) References Cited

U.S. PATENT DOCUMENTS 9,033,506 B2    5/2015   Donitzky et al.
2005/0240147 A1*  10/2005   Makower ............. A61B 18/042
                                                  623/1.11

(Continued)

FOREIGN PATENT DOCUMENTS

KR   10-2001-0053001 A    6/2001
KR   10-2004-0095489 A    11/2004

(Continued)

*Primary Examiner* — Aurelie H Tu
(74) *Attorney, Agent, or Firm* — Bridgeway IP Law Group, PLLC; Sang Ho Lee; Hyun Woo Shin (57) ABSTRACT

An auditory ability test device based on optical coherence tomography of the present disclosure includes: a main console including a light source, a light classifier to classify light emitted from the light source into reference light and measurement light, a coherence signal collector to perform conversion into data from a signal by coherence of reference reflected light and measurement reflected light corresponding to reflection of the reference light and the measurement light respectively, and a calculator to calculate a 3-dimensional structure of a hearing organ and measure an auditory ability according to the data; a reference end to receive the reference light through an optical fiber connected to the light classifier and transmit the reference reflected light generated through a reflector to the main console; and a measurement end to receive the measurement light at one end through an (Continued)

optical fiber connected to the light classifier and generate a sound inside, the measurement end being inserted into the hearing organ through a speculum coupled to the other end to emit the sound and the measurement light and transmit the measurement reflected light reflected from the hearing organ to the main console.

9 Claims, 11 Drawing Sheets

(56) References Cited

U.S. PATENT DOCUMENTS

| | | |
|---|---|---|
| 2011/0098551 A1 | 4/2011 | Zhang |
| 2012/0172893 A1 | 7/2012 | Taylor et al. |
| 2013/0060131 A1* | 3/2013 | Oghalai ............. A61B 1/00165 600/425 |
| 2020/0397247 A1* | 12/2020 | Talbert ............... A61B 1/00006 |
| 2021/0080246 A1* | 3/2021 | Courteville ........ G01B 9/02083 |

FOREIGN PATENT DOCUMENTS

| | | |
|---|---|---|
| KR | 10-2009-0049106 A | 5/2009 |
| KR | 10-2014-0132786 A | 11/2014 |
| KR | 10-1662624 B1 | 10/2016 |
| KR | 10-2017-0050031 A | 5/2017 |
| KR | 10-2018-0027975 A | 3/2018 |
| WO | 96-39924 A1 | 12/1996 |
| WO | 2011/046378 A2 | 4/2011 |

* cited by examiner

AUDITORY ABILITY TEST DEVICE AND METHOD BASED ON OPTICAL COHERENCE TOMOGRAPHY

TECHNICAL FIELD

The present disclosure relates to an auditory ability test device and method based on optical coherence tomography, and more particularly, to an auditory ability test device and method based on optical coherence tomography for calculating the structure of the hearing organ and measuring the auditory ability using light and sound in combination.

BACKGROUND ART

The ear includes the outer ear, the middle ear and the inner ear, the outer ear, also called the earhole, is a pathway running from the earflap to the eardrum and includes the auditory canal, the middle ear includes the hammer, the anvil and the stirrup internal to the eardrum, and the inner ear includes the oval window, the semicircular canals, the cochlea and the auditory nerve.

Conventionally, to identify the structure of the ear in which the outer ear is physically separated from the middle ear and the inner ear by the eardrum, the structure of the outer ear is restrictively identified by inserting a small camera into the auditory canal, and the body temperature is measured by emitting the light source to the eardrum. As described above, the conventional art fails to accurately identify the structure of the middle ear or the inner ear and measure the auditory ability by directly detecting vibration of the auditory ossicles based on the identified structure.

RELATED LITERATURES

Patent Literatures

Korean Patent Publication No. 10-2017-0050031

DISCLOSURE

Technical Problem

The present disclosure is designed to address this issue and therefore the present disclosure is directed to providing an auditory ability test device and method based on optical coherence tomography for calculating the 3-dimensional structure of the inner ear internal to the eardrum.

The present disclosure is further directed to providing an auditory ability test device and method based on optical coherence tomography for measuring the auditory ability through different vibrations of the eardrum or the auditory ossicles depending on the frequency divided into different ranges.

Technical Solution

An auditory ability test device based on optical coherence tomography according to an embodiment of the present disclosure includes: a main console including a light source, a light classifier to classify light emitted from the light source into reference light and measurement light, a coherence signal collector to perform conversion into data from a signal by coherence of reference reflected light and measurement reflected light corresponding to reflection of the reference light and the measurement light respectively, and a calculator to calculate a 3-dimensional (3D) structure of a hearing organ and measure an auditory ability according to the data; a reference end to receive the reference light through an optical fiber connected to the light classifier and transmit the reference reflected light generated through a reflector to the main console; and a measurement end to receive the measurement light at one end through an optical fiber connected to the light classifier and generate a sound inside, the measurement end being inserted into the hearing organ through a speculum coupled to the other end to emit the sound and the measurement light and transmit the measurement reflected light reflected from the hearing organ to the main console.

Additionally, the measurement end may include a 2D optical path controller to convert the measurement light to a plurality of parallel lights, a sounder to output the sound set to a uniform initial frequency inside to vibrate an inside of the hearing organ, and transmit the parallel light and the sound to the hearing organ, and a vibration damper positioned between the 2D optical path controller and the sounder to block vibration generated when the sound is outputted from the sounder.

Additionally, the 2D optical path controller may include a collimator to allow the measurement light transmitted from the light classifier pass therethrough to convert the measurement light to the parallel light, at least one reflector to change a path of the parallel light converted by the collimator to a direction parallel to the speculum, and an objective lens to focus the parallel light converted by the reflector.

Additionally, the sounder may output the parallel light transmitted from the 2D optical path controller and the sound outputted from the inside to the hearing organ through the speculum, and may have a corn shaped end to which the speculum is coupled.

Additionally, the vibration damper may be a tubular structure in which a passage for the parallel light goes through a center, and an entire outer wall contacts the 2D optical path controller and the sounder.

Additionally, the vibration damper may be a radial structure in which a passage for the parallel light goes through a center, and a part of an outer wall is open to release the vibration generated from the sounder.

Additionally, the calculator may track a reflection location of the measurement reflected light by Fourier transform of the coherent data.

Additionally, the calculator may calculate the 3D structure of the hearing organ by considering the reflection location of the measurement reflected light.

Additionally, the calculator may measure the vibration inside the hearing organ generated by the output sound using a complex number in the Fourier transformed result value.

Additionally, in the measurement end, after vibration measurement is completed by emitting the measurement light to the hearing organ vibrating by the initial frequency, the sounder may re-transmit the sound of a different frequency from the initial frequency to induce the hearing organ to vibrate, re-emit the measurement light to the vibrating hearing organ and transmit the measurement reflected light reflected from the hearing organ to the main console, and the calculator may measure the auditory ability for each frequency by comparing the measurement reflected light reflected from the vibration generated by the initial frequency with the measurement reflected light reflected from the vibration generated by the sound of a different frequency from the initial frequency.

An auditory ability test method based on optical coherence tomography according to an embodiment of the present disclosure includes a measurement preparation step of inserting an auditory ability test device into an auditory canal to transmit a sound and light into a hearing organ through the auditory canal, a sound output step of outputting the sound of a preset condition into the hearing organ to induce vibration inside the hearing organ, a light output step of splitting the light emitted in the preset condition by the auditory ability test device into reference light and measurement light, and outputting the measurement light into the hearing organ vibrating through the sound output step, and a reflected light analysis step of receiving the measurement reflected light for the measurement light outputted in the light output step, reflected from the hearing organ vibrating in response to the sound, calculating a structure of the hearing organ based on the received measurement reflected light, and measuring a phase change of the measurement reflected light.

Additionally, the sound output step may include outputting a sound signal inputted through a central processing device connected to the auditory ability test device to the hearing organ.

Additionally, the sound output step may include focusing the sound outputted from a plurality of sounders included in the auditory ability test device to one point and transmitting to the hearing organ.

Additionally, the light output step may include converting the measurement light to a plurality of parallel lights, and controlling a path of the converted measurement light to a direction parallel to the auditory canal to focus each measurement light converted to the plurality of parallel lights to different regions inside the vibrating hearing organ.

Additionally, the light output step may include setting a path of the reference light to generate the reference reflected light free of a phase change and induce the reference reflected light to return back.

Additionally, the reflected light analysis step may include collecting a coherence signal by coherence of the reference reflected light and the measurement reflected light, the coherence signal being proportional to a wavenumber of the light source, a spectrum signal size of the light source and intensity of the reference reflected light and the measurement reflected light.

Additionally, the reflected light analysis step may include calculating the structure of the hearing organ by tracking a reflection location of the reflected light by performing Fourier transform on the collected coherence signal.

Additionally, the reflected light analysis step may include measuring a phase change of the measurement reflected light through a phase value acquired according to a result in a complex number form calculated by performing Fourier transform on the collected coherence signal.

Additionally, the reflected light analysis step may include terminating the auditory ability measurement, when vibration analysis of the measurement reflected light for the sound having a single frequency is required.

Additionally, the reflected light analysis step may include independently measuring the vibration of the measurement reflected light reflected from regions in which the vibration occurred by the sound having different frequencies independently outputted to the hearing organ in the sound output step, when vibration analysis of the measurement reflected light for a plurality of sounds having different frequencies is required.

Advantageous Effects

The auditory ability test device based on optical coherence tomography according to the present disclosure calculates the 3-dimensional (3D) structure of the outer ear and the middle ear in the hearing organ and measures the auditory ability in a noncontact and nondestructive manner by optical coherence of sound-induced vibration of the eardrum and the auditory ossicles using continuous-wave broadband light.

Additionally, the auditory ability test device based on optical coherence tomography according to the present disclosure may include the vibration damper to prevent vibration generated when sound is outputted through the sounder from being transmitted to the 2D optical path controller, and may change the shape of the vibration damper depending on the output sound, thereby achieving the auditory ability test device with improved stability.

Additionally, the auditory ability test device based on optical coherence tomography according to the present disclosure calculates the 3D structure through the calculator, and represents and outputs the level of vibration according to the reflection location of the 3D structure in greyscale brightness or feature patterns of colors, thereby making it possible to intuitively see the test result.

Additionally, the quantitative measurement of the response of the hearing organ through the auditory ability test device based on optical coherence tomography according to the present disclosure may be effectively used to evaluate the auditory ability and select the specification of hearing aids or hearing implants, and thus may be applied to the markets of hearing test equipment and hearing aids relying on the indirect test, thereby covering a wide range of markets.

BEST MODE

The following detailed description of the present disclosure is made with reference to the accompanying drawings, in which particular embodiments for practicing the present disclosure are shown for illustration purposes. These embodiments are described in sufficiently detail for those having ordinary skill in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, the preferred embodiments of the present disclosure will be described in more detail with reference to the accompanying drawings.

An auditory ability test device based on optical coherence tomography according to the present disclosure may calculate a 3-dimensional (3D) structure of the outer ear and the middle ear in the hearing organ and measure the auditory ability in a noncontact and nondestructive manner by coherence of sound-induced vibration of the eardrum and the auditory ossicles using continuous-wave broadband light.

Figure 1:
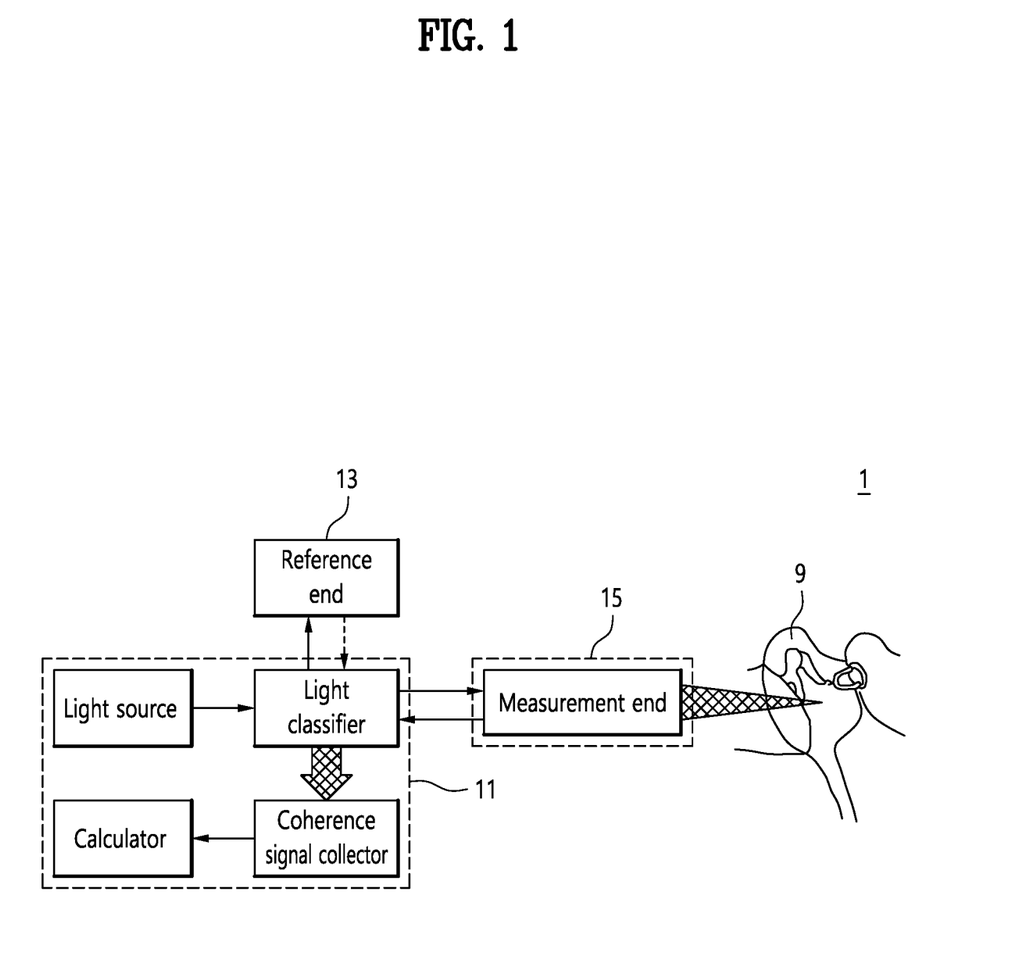
FIG. 1 is a diagram of an auditory ability test device based on optical coherence tomography according to an embodiment of the present disclosure.

FIG. 1 is a diagram of an auditory ability test device based on optical coherence tomography according to an embodiment of the present disclosure.

Referring to FIG. 1, the auditory ability test device based on optical coherence tomography according to an embodiment of the present disclosure (hereinafter the auditory ability test device) 1 includes a main console 11, a reference end 13 and a measurement end 15.

The main console 11 may be connected to the reference end 13 and the measurement end 15 through different optical fibers. The main console 11 may calculate a 3D structure of a hearing organ 9 or measure the auditory ability by coherence of reference reflected light and measurement reflected light returning back to the reference end 13 and the measurement end 15. The quantitative value of the 3D structure or the auditory ability calculated by the main console 11 may be outputted through an external display device. Additionally, a user may adjust the measurement conditions such as the bandwidth of the output light and the frequency of sound through manipulation of the main console 11.

To this end, the main console 11 may include a light source 111, a light classifier 113, a coherence signal collector 115 and a calculator 117. Each component of the main console 11 will be described in detail through FIG. 2.

The reference end 13 may receive reference light through the optical fiber connected to the light classifier 113. The reference end 13 may reflect the reference light through an object such as a mirror and a reflector on the other side where the reference light is received, to generate reference reflected light and transmit the reference reflected light to the main console 11. The reference reflected light generated through the reference end 13 does not require a phase change, and may be used to determine a change in phase from the measurement reflected light at the same phase as the reference light.

The measurement end 15 may receive measurement light at one end through the optical fiber connected to the light classifier 113. The measurement end 15 may generate a sound inside. The measurement end 15 may be inserted into the hearing organ 9 through a speculum 1531 coupled to the other end to emit the sound and the measurement light. The measurement end 15 may transmit the measurement reflected light reflected from the hearing organ 9 to the main console 11.

Meanwhile, each component of the measurement end 15 and the path of the measurement light will be described in detail through FIGS. 3 to 7.

Figure 2:
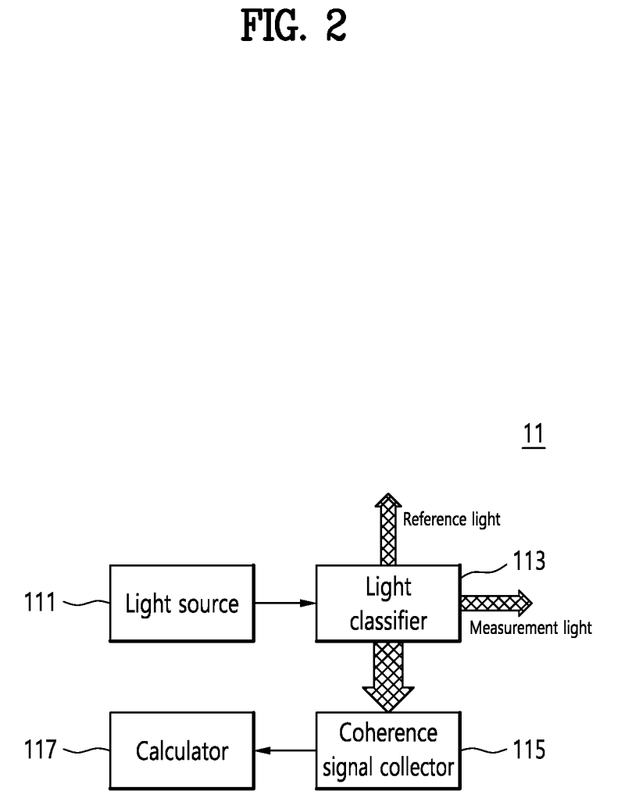
FIG. 2 is a diagram of a main console of the auditory ability test device based on optical coherence tomography of FIG. 1.

FIG. 2 is a diagram of the main console of the auditory ability test device based on optical coherence tomography of FIG. 1.

Referring to FIG. 2, the main console 11 may include the light source 111, the light classifier 113, the coherence signal collector 115 and the calculator 117. The light source 111 may output continuous-wave low-coherence light. The light source 111 may output broadband light having a uniform bandwidth on the basis of the center wavelength. The light outputted though the light source 111 may be transmitted to the light classifier 113.

The light classifier 113 may classify the light from the light source 111 into reference light and measurement light. The light classifier 113 may transmit the reference light to the reference end 13 and the measurement light to the measurement end 15. The light classifier 113 may induce optical coherence of the reference reflected light and the measurement reflected light returning back to the reference end 13 and the measurement end 15. The light classifier 113 may transmit a signal induced by optical coherence to the coherence signal collector 115.

The coherence signal collector 115 may perform conversion into data from the coherence signal of the reference reflected light and the measurement reflected light corresponding to the reflection of the reference light and the measurement light respectively. The coherence signal collector 115 may perform digitization to enable a system such as a computer device to process the signal converted into data. The coherence signal collector 115 may transmit information transformed from the data to the calculator 117.

The calculator 117 may calculate the 3D structure of the hearing organ 9 and measure the auditory ability according to the data received from the coherence signal collector 115. The calculator 117 may track the reflection location of the measurement reflected light by Fourier transform of the coherent data by the coherence signal collector 115. The calculator 117 may calculate the 3D structure of the hearing organ 9 by considering the reflection location of the measurement reflected light. In particular, the calculator 117 may calculate the 3D structure of the outer ear or the middle ear. The calculator 117 may measure vibration inside the hearing organ 9 generated by the output sound using a complex number in the Fourier transformed result value. In detail, the calculator 117 may measure vibration of the eardrum or the auditory ossicles.

Figure 3:
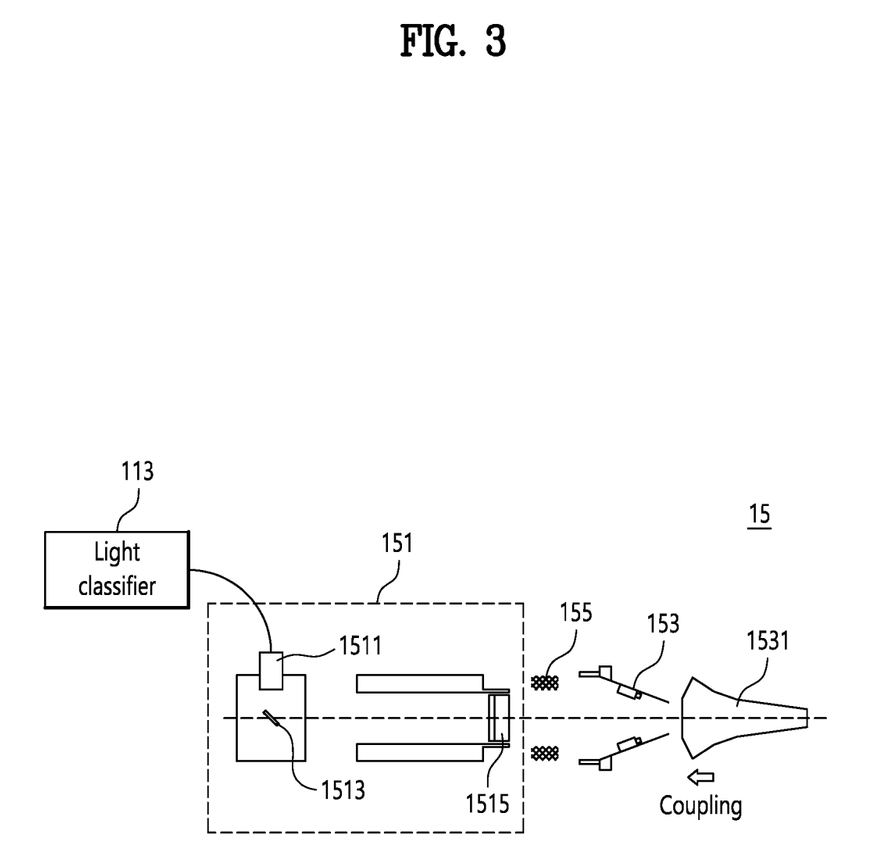
FIG. 3 is a diagram of a measurement end of the auditory ability test device based on optical coherence tomography of FIG. 1.

FIG. 3 is a diagram of the measurement end of the auditory ability test device based on optical coherence tomography of FIG. 1.

Referring to FIG. 3, the measurement end 15 may include a 2D optical path controller 151, a sounder 153 and a vibration damper 155. The 2D optical path controller 151 may receive the measurement light from the light classifier 113. The 2D optical path controller 151 may convert the measurement light into a plurality of parallel lights. The 2D optical path controller 151 may transmit the parallel light to the sounder. To this end, the 2D optical path controller 151 may include a collimator 1511, a reflector 1513 and an objective lens 1515.

The collimator 1511 may allow the measurement light transmitted from the light classifier 113 to pass therethrough to convert the measurement light to the parallel light. The collimator 1511 may convert the measurement light transmitted along a single path to the plurality of parallel lights having parallel paths. The plurality of parallel lights converted through the collimator 1511 may be reflected off different regions of the auditory ossicles through the eardrum and converted to the measurement reflected light having different phases.

The reflector 1513 may change the path of the parallel light converted by the collimator 1511 to a direction parallel to the speculum 1531. A plurality of reflectors 1513 may be provided to set the path of the parallel light. The reflector 1513 may set the path of the parallel light without changing the phase of the parallel light.

The objective lens 1515 may focus the parallel light converted by the reflector 1513. The objective lens 1515 may refract the plurality of parallel lights having the changed path to focus the parallel lights along the path parallel to the auditory canal. The plurality of parallel lights refracted through the objective lens 1515 may avoid a collision with the sounder 153 or the speculum 1531. Additionally, the plurality of parallel lights refracted through the objective lens 1515 may reach and bounce off different points of the hearing organ 9. In this instance, each of the measurement reflected lights reflected from different points may be different in information such as the return-back time, the return-back phase and the return-back frequency, and the information may be used as data for measuring the 3D structure or the auditory ability of the hearing organ 9 by comparison with the reference reflected light.

The sounder 153 may output sound set to a uniform initial frequency inside to vibrate the inside of the hearing organ 9. The sounder 153 may transmit the parallel light and the sound to the hearing organ 9. The sounder 153 may include a plurality of small speakers, and the speakers may be arranged with high density such that the output direction is set to a direction connected to the speculum 1531. A sound signal outputted from the sounder 153 may be set through an external device and transmitted through a digital analog converter.

Additionally, the sounder 153 may output the parallel light transmitted from the 2D optical path controller 151 and the sound outputted from the inside to the hearing organ 9 through the speculum 1531. The sounder 153 may have a corn shaped end to which the speculum 1531 is coupled. Through this structural feature, the sounder 153 may focus and output the output sound signal to one point. In particular, the speculum 1531 is a replaceable and disposable auxiliary tool, and may prevent the direct contact between the measurement end 15 and the human body, and form a passage to effectively transmit the measurement light and the sound to the hearing organ 9.

The vibration damper 155 may be positioned between the 2D optical path controller 151 and the sounder 153. The vibration damper 155 may block the vibration generated when the sounder 153 outputs the sound. The vibration damper 155 may be provided in different forms depending on the sound outputted from the sounder 153 and positioned between the 2D optical path controller 151 and the sounder 153. Its detailed description will be provided through FIGS. 4A and 4B.

Figure 4A:
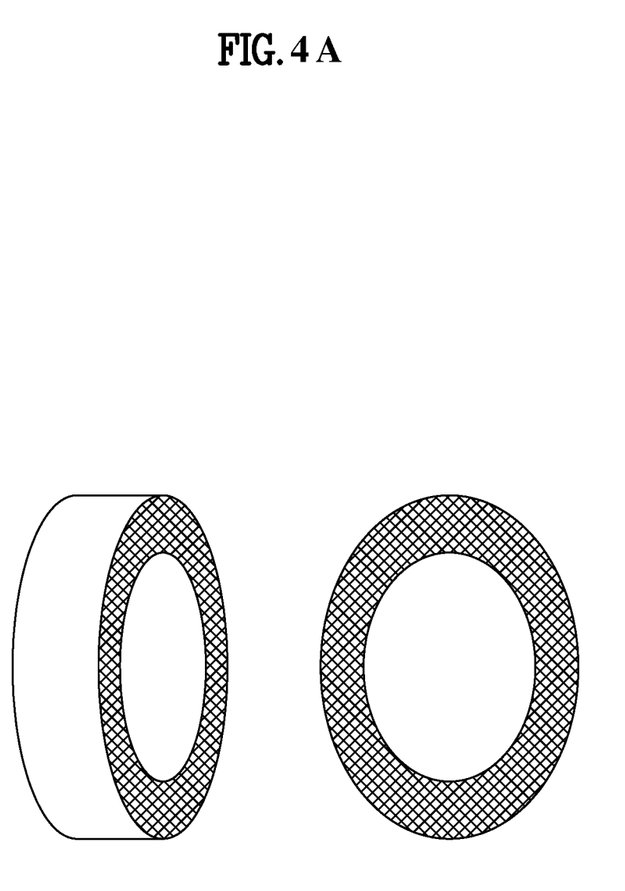
FIGS. 4A and 4B show examples of a vibration damper of the auditory ability test device based on optical coherence tomography of FIG. 1.
Figure 4B:
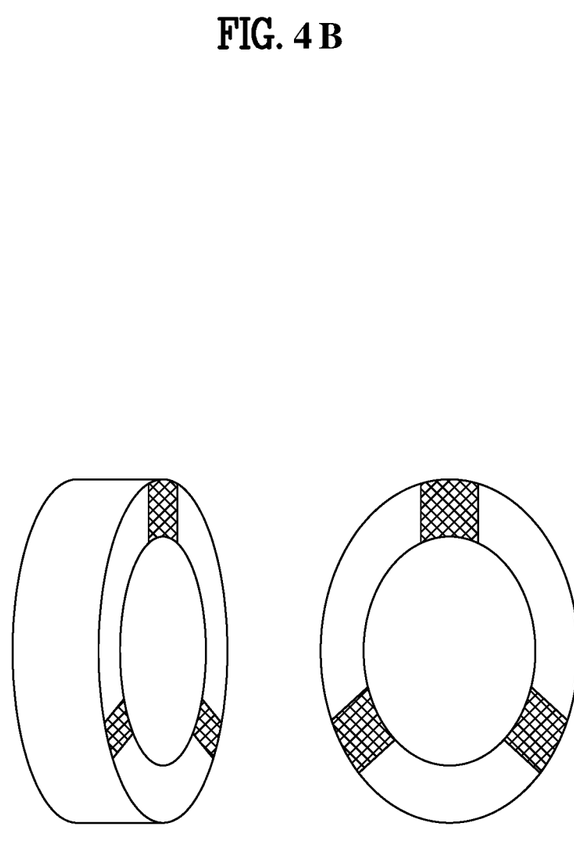

FIGS. 4A and 4B show examples of the vibration damper of the auditory ability test device based on optical coherence tomography of FIG. 1.

Referring to FIG. 4A, the vibration damper may be a tubular structure in which the passage for the parallel light goes through the center, and the entire outer wall contacts the 2D optical path controller 151 and the sounder 153. This type vibration damper may maximize the contact surface with the 2D optical path controller 151 and the sounder 153 and increase the coupling strength, thereby improving the stability of the auditory ability test device 1.

Additionally, referring to FIG. 4B, the vibration damper may be a radial structure in which the passage for the parallel light goes through the center and a part of the outer wall is open to release the vibration generated from the sounder 153. This type vibration damper may minimize the contact surface with the sounder 153, and induce the circulation of air through the area except the contact surface to minimize the transmission of vibration caused by the sound outputted from the sounder 153, thereby reducing the movement of the 2D optical path controller 151.

As described above, the vibration damper 155 may be provided with various structures to achieve the structural stability or reduced vibration transmission, and may be provided in altered forms to ensure design modification and stability.

Figure 5:
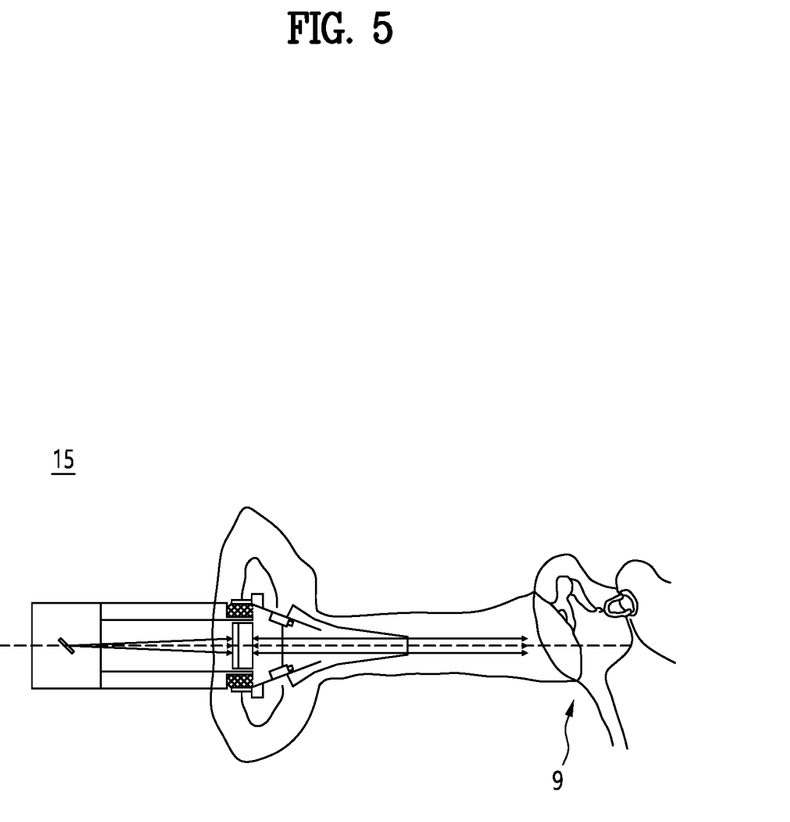
FIGS. 5 to 7 are diagrams for describing a process of calculating the structure of a hearing organ and measuring the auditory ability through a measurement end of an auditory ability test device based on optical coherence tomography.
Figure 6:
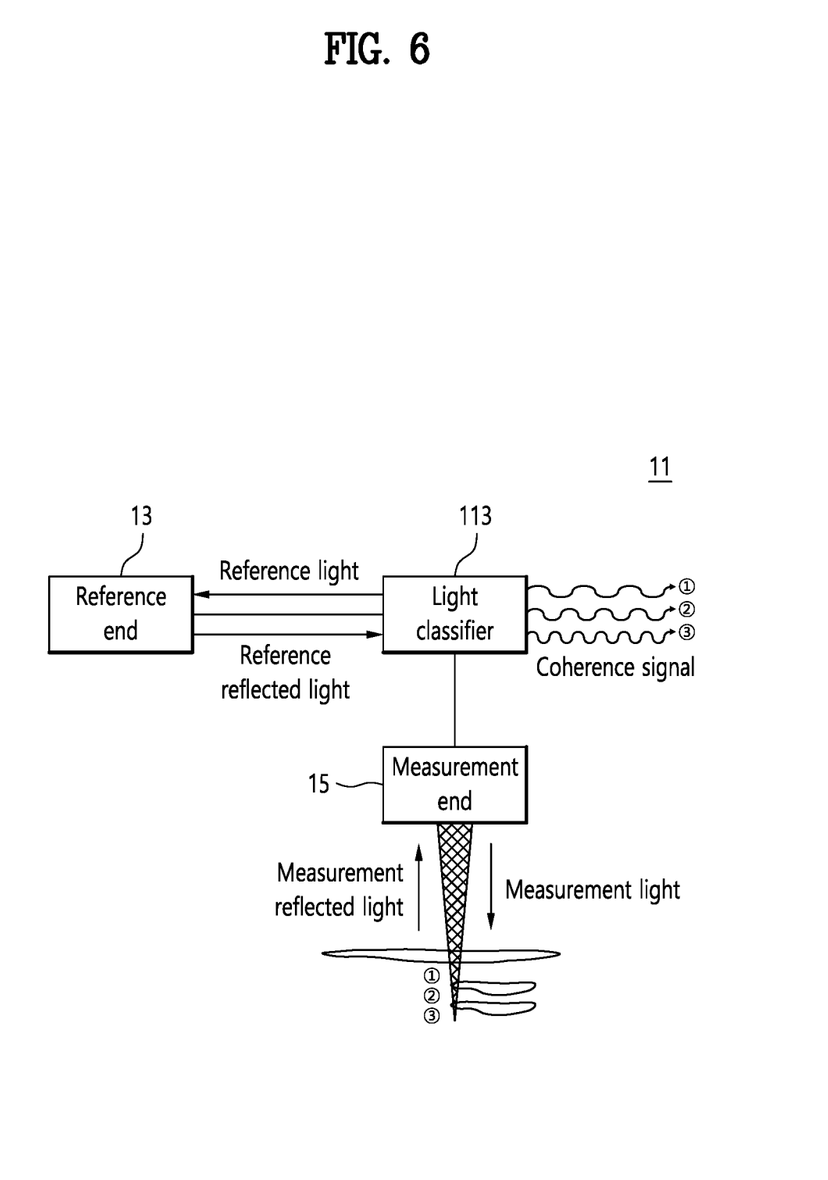
Figure 7:
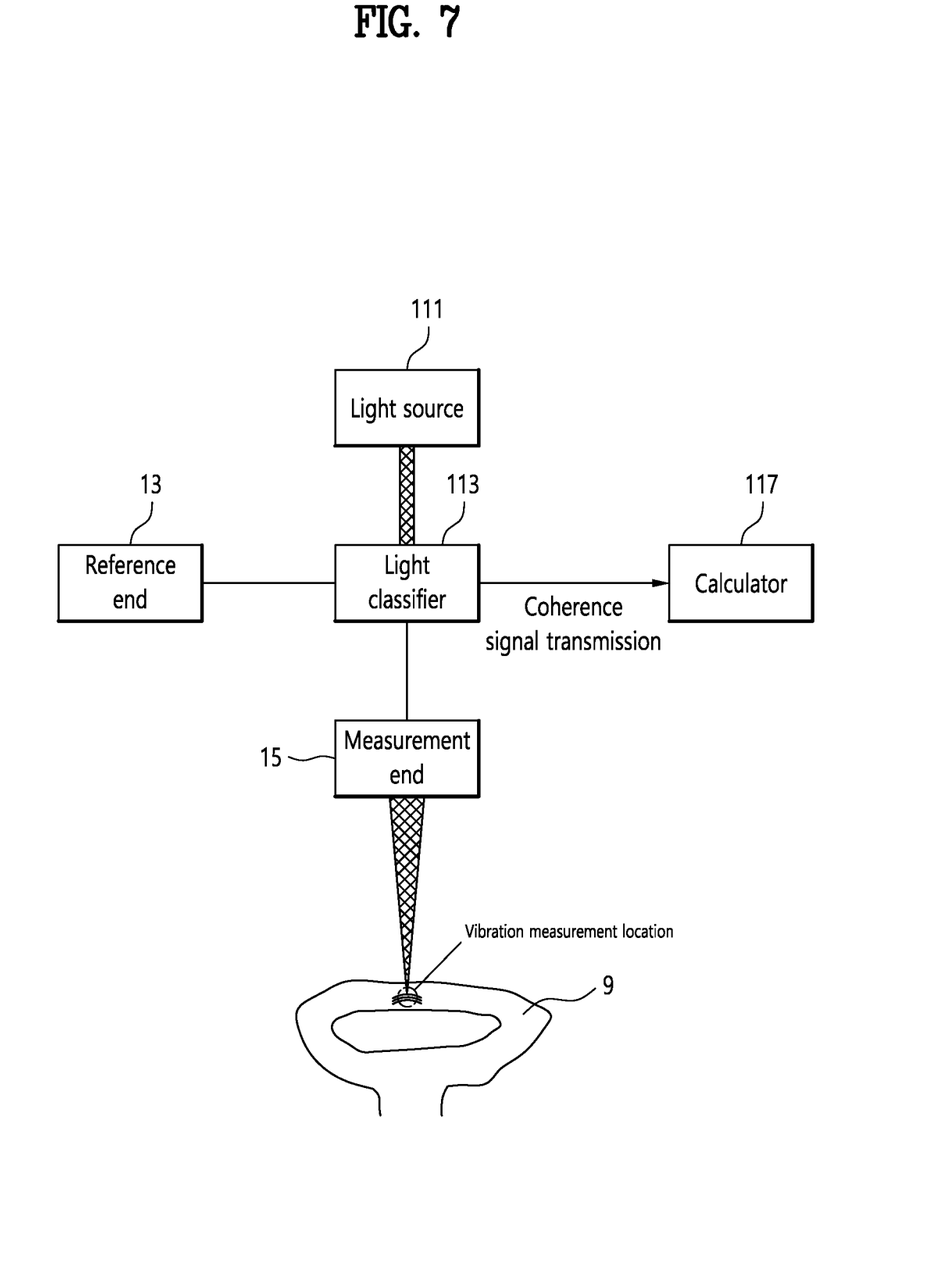

FIGS. 5 to 7 are diagrams for describing a process of calculating the structure of the hearing organ and measuring the auditory ability through the measurement end of the auditory ability test device based on optical coherence tomography.

Referring to FIGS. 5 to 7, the speculum 1531 may be attached to the tip of the measurement end 15 and inserted into the auditory canal, and test sound may be set and outputted to the hearing organ 9. Subsequently, in the measurement end 15, after vibration measurement is completed by emitting the measurement light to the hearing organ 9 vibrating by the initial frequency, the sounder 153 may re-transmit sound of a different frequency from the initial frequency to induce the hearing organ 9 to vibrate, re-emit the measurement light to the vibrating hearing organ 9 and transmit the measurement reflected light reflected from the hearing organ 9 to the main console 11. As described above, the measurement end 15 may emit the measurement light and the sound, re-collect the measurement reflected light reflected from the hearing organ 9 and re-transmit to the main console 11. Additionally, the vibration re-collected through the measurement end 15 may be measured and stored independently for each sound selected through the calculator 117.

Subsequently, the calculator 117 may measure the auditory ability for each frequency of the output sound by comparing the measurement reflected light reflected by the vibration generated by the initial frequency with the measurement reflected light reflected by the vibration generated by the sound of a different frequency from the initial frequency.

Figure 8:
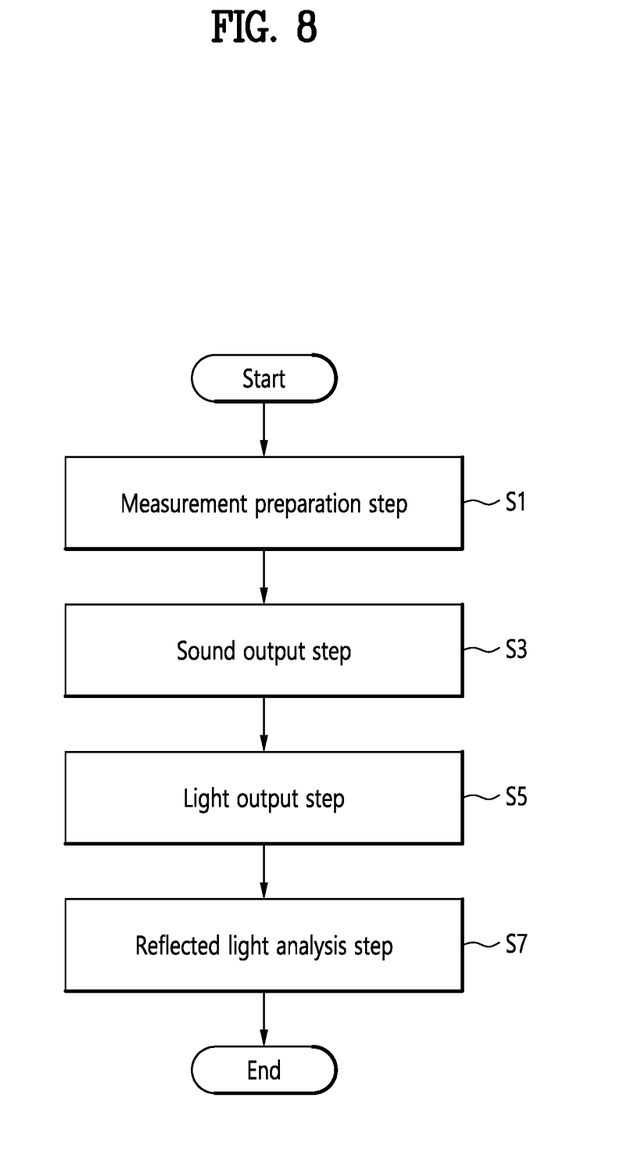
FIG. 8 is a flowchart of an auditory ability test method based on optical coherence tomography according to an embodiment of the present disclosure.
Figure 9:
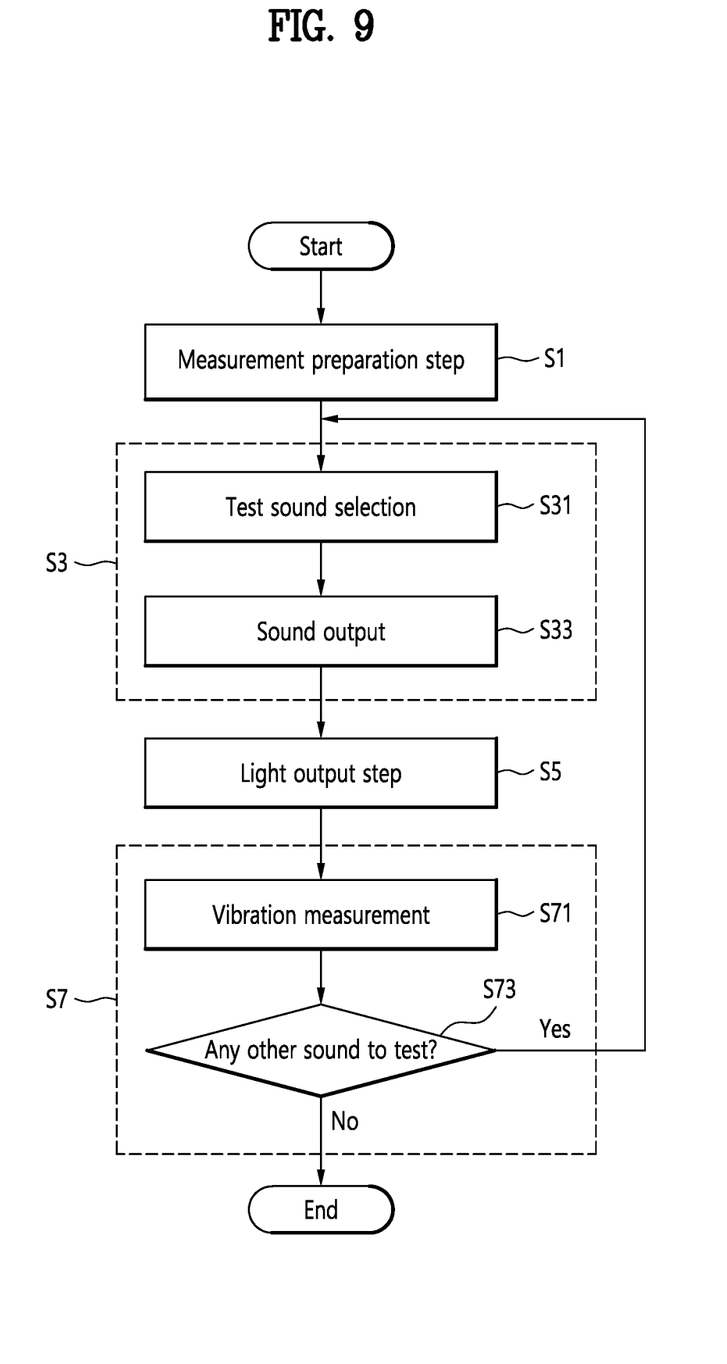
FIG. 9 is a flowchart detailing the sound output step and the reflected light analysis step of the auditory ability test method of FIG. 8.
Figure 10:
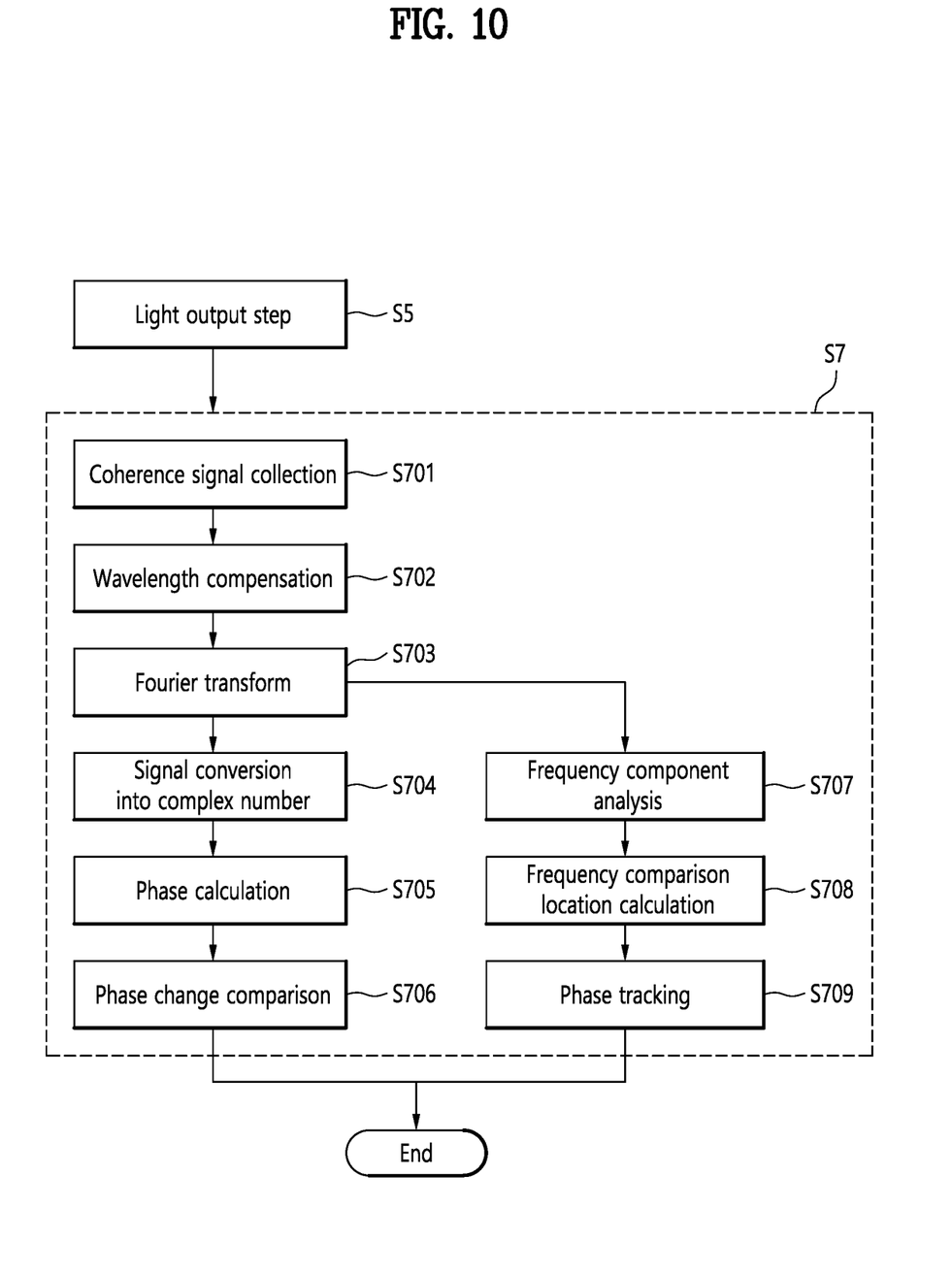
FIG. 10 is a flowchart detailing the reflected light analysis step of the auditory ability test method of FIG. 8.

FIG. 8 is a flowchart of an auditory ability test method based on optical coherence tomography according to an embodiment of the present disclosure, FIG. 9 is a flowchart detailing the sound output step and the reflected light analysis step of the auditory ability test method of FIG. 8, and FIG. 10 is a flowchart detailing the reflected light analysis step of the auditory ability test method of FIG. 8.

Referring to FIGS. 8 to 10, the auditory ability test method based on optical coherence tomography according to an embodiment of the present disclosure includes a measurement preparation step S1, a sound output step S3, a light output step S5 and a reflected light analysis step S7.

In the measurement preparation step S1, the auditory ability test device may be inserted into the auditory canal. In the measurement preparation step S1, the auditory ability test device may be set to transmit sound and light into the hearing organ.

In detail, in the measurement preparation step S1, the speculum may be mounted on the measurement end of the auditory ability test device. In the measurement preparation step S1, the auditory ability test device may be inserted such that sound or light is outputted in a direction parallel to the auditory canal.

In the sound output step S3, sound of a preset condition may be outputted into the hearing organ to induce vibration into the hearing organ. The sound output step S3 may include the step S31 of selecting the frequency of test sound and the step S33 of outputting the sound of the selected frequency. Through this, in the sound output step S3, a sound signal inputted through a central processing device connected to the auditory ability test device may be outputted to the hearing organ.

In detail, in the sound output step S3, sound of a desired frequency may be selected to receive the input sound signal of the corresponding frequency through the central processing device. The selected frequency may be a single frequency or different frequencies, and various frequencies may be selected according to the purpose of measurement and the input sound signal may be received.

Subsequently, in the sound output step S3, the sound outputted from the plurality of sounders included in the auditory ability test device may be focused to one point and transmitted to the hearing organ. As the sound outputted in different directions from the plurality of sounders included in the auditory ability test device may individually reach the same point according to the position and placement of the sounders, in the sound output step S3, the sound outputted from the plurality of sounders may be focused to one point to transmit a single sound to the hearing organ. Through this, sound having a single frequency may be transmitted to the hearing organ through a single path, to induce a single vibration to the hearing organ, thereby improving the reliability of the auditory ability test.

In the light output step S5, the light emitted in a preset condition by the auditory ability test device may be split into reference light and measurement light. In the light output step S5, the measurement light may be outputted into the hearing organ vibrating through the sound output step S3. In the light output step S5, the path of the reference light may be set to generate reference reflected light free of a phase change. In the light output step S5, the reference reflected light may be induced to return back. In the light output step S5, the path of the reference light may be set to generate reference reflected light free of a phase change. In the light output step S5, the reference reflected light may be induced to return back.

In detail, in the light output step S5, the light may be split to compare the measurement reflected light for the measurement light reflected from the hearing organ with the reference reflected light for the reference light reflected inside of the auditory ability test device in the reflected light analysis step S7, and the reference reflected light may be set as a control.

In the light output step S5, the measurement light may be converted to a plurality of parallel lights, and the path of the converted measurement light may be controlled to a direction parallel to the auditory canal. In the light output step S5, each measurement light converted to the plurality of parallel lights may be focused to different regions inside the vibrating hearing organ.

In detail, the plurality of parallel lights converted in the light output step S5 may be focused to different locations and reflected back, and in the reflected light analysis step S7, the structure of the hearing organ or the auditory ability may be measured through the measurement reflected light differently reflected back.

In the reflected light analysis step S7, the measurement reflected light may be received, the measurement reflected light being the reflection of the measurement light outputted in the light output step S5 from the hearing organ that vibrates in response to the sound. In the reflected light analysis step S7, the structure of the hearing organ may be calculated based on the received measurement reflected light. In the reflected light analysis step S7, a phase change of the measurement reflected light may be measured.

In the reflected light analysis step S7, a coherence signal by coherence of the reference reflected light and the measurement reflected light may be collected, and the coherence signal may be proportional to the wavenumber of the light source, the spectrum signal size of the light source and the intensity of the reference reflected light and the measurement reflected light.

In detail, the coherence signal collected in the reflected light analysis step S7 may be represented as the following [Equation 1].

$$I_D(k) = S(k)\{[R_R + R_S] + 2\sqrt{R_R R_S} \cos(2\Delta z k)\} \quad \text{[Equation 1]}$$

Here, K denotes the wavenumber and is inversely proportional to the wavelength λ. S(k) denotes the spectrum signal size of the light source, and $R_R$ and $R_S$ denote the intensity of the reference reflected light and the measurement reflected light corresponding to the reflection of the reference light and the measurement light respectively. Additionally, Δz denotes a distance difference between a reference mirror from which the reference light is reflected and a sample from which the measurement light is reflected.

Subsequently, in the reflected light analysis step S7, the structure of the hearing organ may be calculated by tracking the reflection location of the reflected light by performing Fourier transform on the collected coherence signal. Additionally, in the reflected light analysis step S7, a phase change of the measurement reflected light may be measured through a phase value acquired according to the result in the form of a complex number, calculated by performing Fourier transform on the collected coherence signal.

In detail, the following [Equation 2] may be obtained by modifying the above [Equation 1].

$$I_D(z) = \hat{S}(z) \times \{[R_R + R_S]\delta(z) + 2\sqrt{R_R R_S}(\delta(z - \Delta z)\} \quad \text{[Equation 2]}$$

Here, δ(z) is the Dirac delta function, and Ŝ(z) is the Fourier transform function of the light source spectrum. The reflection location of the reflected light may be tracked through the frequency component Δz.

To sum up, in the reflected light analysis step S7, the coherence signal may be acquired by splitting the light by coherence of the reference reflected light and the measurement reflected light through the coherence signal collector into narrow-band continuous waves (S701). In the reflected light analysis step S7, $I_D(k)$ of [Equation 1] may be generated by performing wavelength compensation on the acquired coherence signal based on the wavenumber k (S702), and may be Fourier transformed (S703). The wavelength compensation performed in the reflected light analysis step S7 may be performed using the wavelength collection feature of the coherence signal collector measured using a shortwave light source within the spectrum wavelength range of the light source.

Subsequently, the Fourier transformed $I_D(z)$ in the reflected light analysis step S7 may be represented in the form of a complex number such as I=a+jb (S704), and the intensity A may be represented as $A=\sqrt{a^2+b^2}$. Additionally, the phase may be calculated as the following [Equation 3] (S705).

$$\angle\phi = \tan^{-1}\frac{b}{a} \quad \text{[Equation 3]}$$

Here, a, b are arbitrary constant values set according to the Fourier transform. Subsequently, the phase may be acquired based on the reflection location z and the phase change may be compared (S706).

Meanwhile, the phase at the location of the eardrum and the auditory ossicles on the reflection side may be changed by vibration having the frequency. That is, when vibration occurs, a phase change may occur. To this end, the frequency component of the vibration may be analyzed (S707), and the frequency comparison location may be calculated (S708). A difference in phase by vibration between $a_1+jb_1$ measured at an arbitrary time at the reflection location and $a_2+jb_2$ continuously measured is calculated (S709) as the following [Equation 4].

$$\Delta\phi = \phi_2 - \phi_1 = \tan^{-1}\frac{b_2}{a_2} - \tan^{-1}\frac{b_1}{a_1} \quad \text{[Equation 4]}$$
$$= \tan^{-1}\frac{b_2 a_1 - a_2 b_1}{b_1 b_2 + a_1 a_2}$$

The corresponding calculation is the basic calculation for finding the phase difference, and the phase difference to the number of measurement times $f_a$ may be given as the following [Equation 5].

$$f_D = \frac{f_a}{2\pi}\tan^{-1}\frac{b_2 a_1 - a_2 b_1}{b_1 b_2 + a_1 a_2} \quad \text{[Equation 5]}$$

The vibration may be quantitatively represented by calculating 4-Quadrant having the range between $-\pi$ and $\pi$ through [Equation 5], the result of vibration measured based on this may include quantitative values of 3D structure, sound signal specification and vibration level, and the quantitative value of the vibration may be represented and outputted in greyscale brightness and pseudo color and feature patterns on a 3D structure image or an image represented in 2-dimensions to achieve an intuitive test.

Meanwhile, in the reflected light analysis step S7, the structure of the hearing organ or the auditory ability may be analyzed through the vibration measurement step S71, and subsequently, whether to continue testing may be determined by checking information of sound to be tested (S73).

In detail, in the reflected light analysis step S7, when vibration analysis of the measurement reflected light for sound having a single frequency is required, the auditory ability measurement may be terminated. In addition, in the reflected light analysis step S7, when vibration analysis of the measurement reflected light for a plurality of sounds having different frequencies is required, the vibration of the measurement reflected light may be independently measured, the measurement reflected light reflected off regions in which vibration occurred by the sound having different frequencies independently outputted to the hearing organ in the sound output step.

Hereinafter, the auditory ability test device based on optical coherence tomography according to an embodiment of the present disclosure will be described. In the following description, redundant description is omitted in relation to the configuration and features of the auditory ability test method based on optical coherence tomography, and description related to the auditory ability test device based on optical coherence tomography will be further made.

In detail, a coherence signal collected through the coherence signal collector 115 of the main console 11 may be transmitted to the calculator 117, followed by full bandwidth k-domain linearization through wavelength compensation, and then Fourier transform. The calculator 117 may convert the Fourier transformed coherence signal into information through two processing processes.

In an example, the calculator 117 may track each reflection location ①, ②, ③ through Fourier transform of the measurement reflected light having the changed frequency from the measurement light returning back to each reflection location ①, ②, ③ through the 2D optical path controller 151, and construct the 3D structure of the hearing organ by processing the reflection location together with the x-axis and y-axis coordinates.

In another example, the calculator 117 may quantitate the vibration-induced phase displacement of the measurement reflected light according to the reflection location of the measurement light using a complex number obtained as a result of the Fourier transform, and compare the reference reflected light with the Fourier transformed complex number. Through this, the auditory ability may be measured by converting the level of vibration.

As described above, the auditory ability test device based on optical coherence tomography according to the present disclosure may include the vibration damper to prevent vibration generated when sound is outputted through the sounder from being transmitted the 2D optical path controller, and may change the shape of the vibration damper depending on the output sound, thereby providing the auditory ability test device with improved stability.

Additionally, the auditory ability test device based on optical coherence tomography according to the present disclosure may calculate the 3D structure through the calculator, and represent and output the level of vibration in grey scale brightness or feature patterns of colors according to the reflection location of the 3D structure, thereby making it possible to intuitively see the test result.

Additionally, the quantitatively measurement of the response of the hearing organ through the auditory ability test device based on optical coherence tomography according to the present disclosure may be effectively used to evaluate the auditory ability and select the specification of hearing aids or hearing implants, and thus may be applied to the markets of hearing test equipment and hearing aids relying on the indirect test, thereby covering a wide range of markets.

While the present disclosure has been hereinabove described in detail through the representative embodiments, it will be understood by those skilled in the art that various modifications may be made to the disclosed embodiments without departing from the scope of the present disclosure. Therefore, the scope of protection of the present disclosure should not be limited to the disclosed embodiments, and should be defined by all modifications or variations derived from the appended claims and their equivalent concept.

DETAILED DESCRIPTION OF MAIN ELEMENTS

1: Auditory ability test device
11: Main console

111: Light source
113: Light classifier
115: Coherence signal collector
117: Calculator
13: Reference end
15: Measurement end
151: 2D optical path controller
1511: Collimator
1513: Reflector
1515: Objective lens
153: Sounder
1531: Speculum
155: Vibration damper
9: Hearing organ

The invention claimed is:

1. An auditory ability test device based on optical coherence tomography, the auditory ability test device comprising:
a main console comprising:
a light source,
a light classifier configured to classify light emitted from the light source into a reference light and a measurement light,
a coherence signal collector configured to perform conversion of a coherence signal into data, wherein the coherence signal is induced by coherence from reference reflected light and measurement reflected light corresponding to reflection of the reference light and reflection of the measurement light, respectively, and
a calculator configured to generate a 3-dimensional (3D) structure of a hearing organ and measure an auditory ability according to the data;
a reference end configured to receive the reference light through a first optical fiber connected to the light classifier and transmit the reference reflected light generated through a reflector to the main console; and
a measurement end configured to receive the measurement light at one end thereof through a second optical fiber connected to the light classifier, and generate a sound inside of the measurement end,
wherein the measurement end is configured to be inserted into the hearing organ through a speculum coupled to another end of the measurement end, to emit the sound and the measurement light, and to transmit the measurement reflected light reflected from the hearing organ to the main console, and
wherein the measurement end is configured to re-emit another sound of another frequency different from a uniform initial frequency of the sound to induce the hearing organ to vibrate, to re-emit another measurement light to the hearing organ, and to transmit another measurement reflected light reflected from the hearing organ vibrating at the another frequency to the main console, and
wherein the calculator is configured to measure the auditory ability for each frequency by comparing the measurement reflected light reflected from the vibration generated by the uniform initial frequency with the another measurement reflected light reflected from the vibration generated by the another sound of the another frequency.

2. The auditory ability test device of claim 1,
wherein the measurement end comprises:
a 2-dimensional (2D) optical path controller configured to convert the measurement light to a plurality of parallel lights;
a sounder configured to output the sound to the uniform initial frequency to vibrate an inside of the hearing organ, and transmit the plurality of parallel lights and the sound to the hearing organ; and
a vibration damper positioned between the 2D optical path controller and the sounder to block vibration generated when the sound is outputted from the sounder.

3. The auditory ability test device of claim 2,
wherein the 2D optical path controller comprises:
a collimator configured to allow the measurement light transmitted from the light classifier pass therethrough to convert the measurement light to the plurality of parallel lights;
at least one reflector configured to change a path of the plurality of parallel lights converted by the collimator to a direction parallel to the speculum; and
an objective lens configured to focus the plurality of parallel lights converted by the at least one reflector.

4. The auditory ability test device of claim 2,
wherein the sounder is configured to output the plurality of parallel lights converted by the 2D optical path controller and the sound outputted from the inside of the measurement end to the hearing organ through the speculum, and
wherein the sounder has a corn shaped end to which the speculum is coupled.

5. The auditory ability test device of claim 2,
wherein the vibration damper has a tubular structure having a passage through a center thereof for transmission of the plurality of parallel lights, and an entire outer wall of the tubular structure contacts the 2D optical path controller and the sounder.

6. The auditory ability test device of claim 2,
wherein the vibration damper has a radial structure having a passage through a center thereof for transmission of the plurality of parallel lights, and a part of an outer wall of the radial structure is open to release the vibration generated from the sounder.

7. The auditory ability test device of claim 1,
wherein the calculator is configured to track a reflection location of the measurement reflected light by Fourier transform of the data.

8. The auditory ability test device of claim 7,
wherein the calculator is configured to generate the 3D structure of the hearing organ based on the reflection location of the measurement reflected light.

9. The auditory ability test device of claim 7,
wherein the calculator is configured to measure vibration inside the hearing organ generated by the sound using a complex number in a Fourier transformed result value.

* * * * *